US008523862B2

(12) United States Patent
Murashko, Jr.

(10) Patent No.: US 8,523,862 B2
(45) Date of Patent: Sep. 3, 2013

(54) BONE PLATE AIMING BLOCK

(75) Inventor: Alexander Murashko, Jr., Shrewsbury, NJ (US)

(73) Assignee: Stryker Leibinger GmbH & Co. KG (DE)

( * ) Notice: Subject to any disclaimer, the term of this patent is extended or adjusted under 35 U.S.C. 154(b) by 331 days.

(21) Appl. No.: 13/079,302

(22) Filed: Apr. 4, 2011

(65) Prior Publication Data
US 2012/0253347 A1  Oct. 4, 2012

(51) Int. Cl.
*A61B 17/58* (2006.01)

(52) U.S. Cl.
USPC ............................ 606/71; 606/96; 408/115 R

(58) Field of Classification Search
USPC ......... 606/70–71, 280–299, 96–98; 403/362, 403/408.1; 408/115 R; 411/45–48; 433/75–76
See application file for complete search history.

(56) References Cited

U.S. PATENT DOCUMENTS

| | | | |
|---|---|---|---|
| 4,828,221 A * | 5/1989 | Scobie et al. | 251/308 |
| 5,364,399 A | 11/1994 | Lowery et al. | |
| 6,066,142 A * | 5/2000 | Serbousek et al. | 606/96 |
| 6,623,486 B1 | 9/2003 | Weaver et al. | |
| 7,316,687 B2 * | 1/2008 | Aikins et al. | 606/70 |
| 7,413,367 B2 * | 8/2008 | Hawang | 403/297 |
| 7,578,825 B2 * | 8/2009 | Huebner | 606/104 |
| 8,162,950 B2 * | 4/2012 | Digeser et al. | 606/96 |
| 2003/0040748 A1 | 2/2003 | Aikins et al. | |
| 2005/0085818 A1 * | 4/2005 | Huebner | 606/69 |
| 2005/0137606 A1 * | 6/2005 | Binder et al. | 606/96 |
| 2007/0167953 A1 * | 7/2007 | Prien et al. | 606/102 |
| 2008/0183172 A1 | 7/2008 | Fritzinger | |
| 2009/0157086 A1 | 6/2009 | Digeser et al. | |
| 2009/0228047 A1 | 9/2009 | Derouet et al. | |
| 2010/0106196 A1 * | 4/2010 | Erickson et al. | 606/281 |

(Continued)

FOREIGN PATENT DOCUMENTS

| | | |
|---|---|---|
| EP | 2072016 A1 | 6/2009 |
| WO | 2005/092224 A1 | 10/2005 |
| WO | 2009121144 A1 | 10/2009 |

OTHER PUBLICATIONS

International Search Report and Written Opinion, PCT/US10/52425, dated Dec. 6, 2010.
European Search Report for EP11184357 dated Jan. 19, 2012.

*Primary Examiner* — Todd Manahan
*Assistant Examiner* — Eric S Gibson
(74) *Attorney, Agent, or Firm* — Lerner, David, Littenberg, Krumholz & Mentlik, LLP

(57) ABSTRACT

A drill guide system for a bone plate having holes includes a guide block having at least two drill guide bores alignable with a bone screw receiving hole in a bone plate. A locking element extending through at least one drill guide block bore into the bone plate bone screw receiving hole, the locking element having a partially threaded bore portion and having a bifurcated tip surrounding the threaded bore portion. The bifurcated tip capable of engaging an inwardly extending protrusion formed on an internal wall of a bone screw receiving hole in the bone plate. An axially moveable threaded rod has a head for contacting an outer surface of the guide block and an end portion engaging a portion of the bore in the bifurcated tip of the locking element for separating sections of the bifurcated tip on axial movement of the rod prior to the head contacting the second surface of the drill guide block.

18 Claims, 6 Drawing Sheets

(56) References Cited

U.S. PATENT DOCUMENTS

| | | | |
|---|---|---|---|
| 2010/0179599 A1* | 7/2010 | Derouet et al. | 606/280 |
| 2011/0106086 A1* | 5/2011 | Laird | 606/70 |
| 2012/0078252 A1* | 3/2012 | Huebner et al. | 606/70 |
| 2012/0191104 A1* | 7/2012 | Jost et al. | 606/102 |
| 2012/0253347 A1* | 10/2012 | Murashko, Jr. | 606/71 |
| 2012/0271310 A1* | 10/2012 | McGee | 606/71 |

* cited by examiner

BONE PLATE AIMING BLOCK

BACKGROUND OF THE INVENTION

The present invention relates to a bone plating system and instrumentation used in the fixation of fractures of long bones such as the femur, tibia, humerus and radius, including periarticular fractures. More specifically, the present invention encompasses a bone plating system that aids in the location of bone screws and drilling of pilot holes for the placement and intraoperative adjustment and fixation of the plate to the fractured bone.

Typical fixation of a fracture of a long bone with a bone plate requires making an incision in the tissue, reducing the fracture, placing a bone plate on the fractured bone, and securing the bone plate to the bone with fixation elements such as screws. The bone plate immobilizes the fracture and keeps the bone in a correct position so as to allow the fracture to heal.

Typically, bone plates have a bone contacting side and a side facing away from the bone with a plurality of holes or apertures extending between the two surfaces. These holes or apertures may be either threaded (for use with locking screws) or non-threaded (for use with regular screws) and may be circular or oblong in shape.

In order to allow for a reliable stabilization of a broken bone in its normal position, special bone stabilizing implants are frequently used. Such implants are for instance metal plates, which are made e.g. from surgical stainless steel or titanium. Plates used for such purposes are usually fixed to the bone parts by means of threaded screws, which are driven into the bone tissue after so-called pre-drilled or pilot-drilled holes have been generated in the bone tissue. These pre-drilled holes allow for a reliable screwing procedure whereby the risk of further destroying the bone with the screw is significantly reduced.

In order to facilitate the drilling of these pre-drilled holes there are known so-called aiming or targeting devices, which work like a drilling jig. Thereby, an aiming or targeting device is detachably fixed to the metal plate in a precise position.

One such bone plate is shown in U.S. Pat. No. 6,623,486 in which the plate has a head portion for placement adjacent the metaphysis of the bone and a shaft portion for placement against the diaphysis of the bone. The plate includes both locking (threaded) holes and non-locking holes. The locking holes are adapted to receive bone screws with threaded heads or proximal areas which engage the threads in the locking holes to thereby lock the screw to the plate. Bone screws without threaded heads can be then inserted into the non-locking holes or into the oblong holes which oblong holes permit the screws to be oriented at various angles.

A drill guide system including a bone plate and aiming block is shown in U.S. Patent Application Publication No. 2009/0157086, the disclosure of which is incorporated herein by reference.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

BRIEF SUMMARY OF THE INVENTION

Various aspects of the present invention are achieved by a drill guide for a bone plate having holes therethrough for receiving bone screws which guide includes a guide block having drill guide bores alignable with at least two bone screw receiving holes in the bone plate. A first locking element extends through a guide block drill guide bore. The first locking element has a tip for engaging a bone screw receiving holes in the bone plate. The tip is selectively expandable to engage and disengage from the bone plate hole. A second locking element is mounted on the guide block and is engageable with a bone plate hole. The second locking element may also have a tip for resiliently engaging walls of the bone plate hole. The tip of the first locking element is bifurcated having a split portion and the first locking element includes an axially moveable rod for expanding the split tip portion the first and second locking elements may be identical.

The first locking element includes a threaded axial bore for receiving the axially moveable rod and wherein the axially moveable rod is threaded whereby rotation of the threaded rod moves the rod into and out of engagement with an internal contact surface around a bone in the split tip portion of the first locking element. The split tip has at least two arms or branches formed by axially extending slots open at a free end of the first locking element tip. The first locking element includes an antirotation pin extending radially, preferably along an axis perpendicular to a guide bore axis, for engaging an anti-rotation feature of the guide block in the form of radially extending open or grooves adjacent each hole.

The second locking element preferably has a central bore and a tip split into at least two branches surrounding the bore wherein the tip has four branches separated by slots open to a free end of the tip. Preferably, the branches have a lip formed adjacent the free end for engaging a reduced diameter area in the bone plate bore wherein the lip has a smaller diameter than a portion of the second locking element extending through the guide block hole.

A method for drilling holes in bone for receiving bone screws includes placing a bone plate having at least two bone screw receiving holes therethrough on a bone. A drill guide block is then placed on the bone plate, the drill guide block has at least two drill guide bores and is placed in alignment with the bone screw receiving holes of the bone plate. The first locking element is inserted into a first of the drill guide bores of the guide block and into engagement with a corresponding first bone screw receiving hole in the bone plate. A second locking element mounted on the drill guide block is inserted into engagement with a hole in the bone plate. A hole is drilled in the bone using a second drill guide bore on the drill guide block and through a second bone screw receiving hole on the bone plate. Once the pilot hole is drilled through one drill guide bore the first locking element can be located in this bore and a hole drilled in the first drill guide bore.

A drill guide system for a bone plate having holes therethrough for receiving bone screws, comprising: a guide block having at least two drill guide bores, each bore alignable with a bone screw receiving hole in a bone plate. The guide block has a first surface for contacting a surface of a bone plate and a second surface opposite the first surface. A locking element is provided extending through a drill guide into the bone plate bone screw receiving bore. The locking element has a bore with a threaded portion and a bifurcated tip for engaging an inwardly extending protrusion on the wall of a bone screw receiving hole in the bone plate. The bifurcated tip has an outwardly extending flange engaging a surface of the bone plate protrusion facing a bone contacting surface of the bone plate. An axially movable rod has a threaded portion mounted in the threaded bore portion of the locking element. The rod has a head engaging the second surface of the guide block and a tip engaging a bore in the tip of the locking element and is capable of spreading sections of the bifurcated tip on axial movement of the rod prior to the rod head contacting the second surface of the aiming block. The axially moveable rod has an outwardly extending stop element for engaging a stop surface on the guide block. The locking element has a stop element extending through a wall of the locking element in a direction transverse to the bore therein into the bore of the guide bore. The locking element stop element is also engagable with a stop element on the axially moveable rod on movement of the rod element head away from the second surface of the guide block. This prevents the rod from being withdrawn from the locking element. The stop element on the locking element may be moveable in the direction transverse to the bore in the locking element such that it engages the stop element on the axially moveable rod in a first position and does not engage the stop element in a second position. In the second position the rod can be removed from the locking element.

An aiming block fixation system for fixing an aiming block to a bone plate comprising: a bone plate having an outer surface, a bone-contacting surface for application to a bone, first and second bone plate holes extending from the outer surface to the bone-contacting surface. The first and second bone plate holes have a circumferential wall including an inwardly extending protrusion. The first bone plate hole extends along a first axis and the second bone plate hole extends along a second axis. An aiming block is provided having an upper surface, a lower surface engageable with the outer surface of the bone plate and a first aiming block bore extending from the upper surface to the lower surface along an axis which is aligned with the first bone plate hole first axis. The aiming block has an additional bore extending from the upper surface to the lower surface having an axis aligned with the second bone plate hole for second axis. A locking element extends through an aiming block bore into the first bone plate hole. The locking element has a bore with a threaded bore portion and having a bifurcated tip portion for selectively engaging the inwardly extending protrusion. An axially moveable rod having a threaded portion mounted in the threaded bore portion of the locking element. The rod has a head with a surface for contacting the outer surface of the aiming block and an end portion for engaging a portion of the locking element bore in the bifurcated tip portion for separating sections of the bifurcated tip during axial movement of the rod prior to the head contacting the outer surface of the aiming block. The first and second bone plate holes may be threaded or non-threaded. The axially moveable rod has an outwardly extending stop element. A moveable stop element is mounted in a wall of the locking element and moveably in a direction transverse, preferably perpendicular, to the locking element bore through and into the locking element bore. The locking element stop element is engagable with the axially moveable rod stop element on movement of the rod element head away from the second surface of the guide block. The second stop element on the locking element is moveable in a direction transverse to the bore in the locking element from a first to a second position and engages the stop element on the axially moveable rod in the first position and does not engage the stop element in the second position. Preferably the bifurcated tip has four sections separated by four axially extending slits extending from the free end of the locking element tip towards the locking element head. The moveable stop element is located between the locking element head and an end of the slits. The moveable stop element has a head portion for engaging an anti-rotation feature in the aiming block bore.

DETAILED DESCRIPTION

Figure 1:
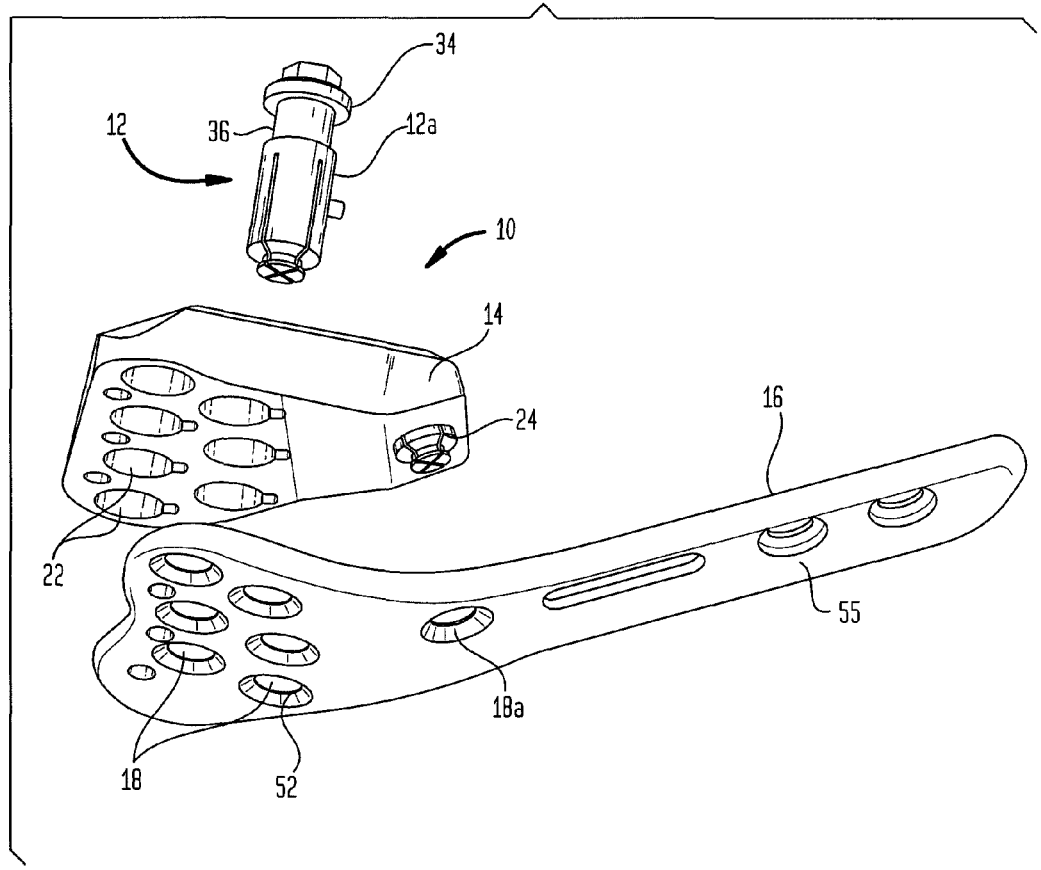
FIG. 1 is an exploded view of the bone plate instrumentation of the present invention including a bone plate, drill guide aiming block and a first locking element adapted to lock the drill guide block to the bone plate.
Figure 1A:
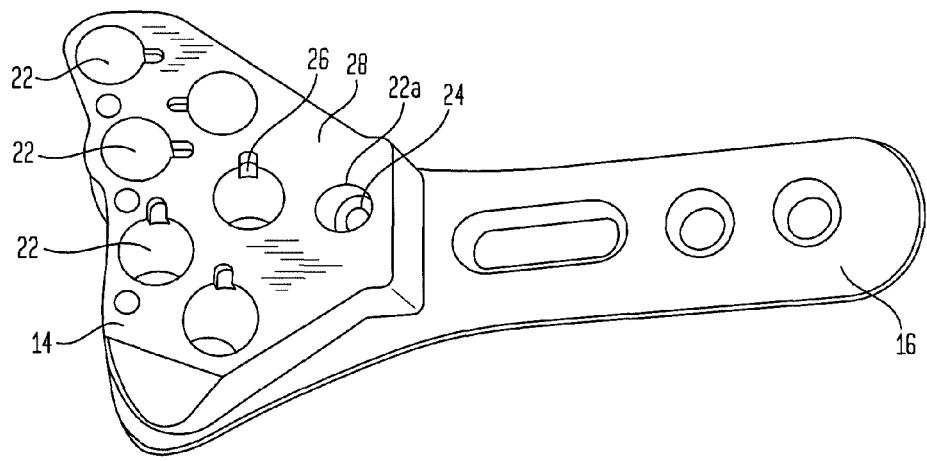
FIG. 1A is a top view of the aiming block placed on top of the bone plate prior to insertion of any locking elements.

Referring to FIGS. 1 and 1A there is shown an exploded view of the instrumentation of the present invention generally denoted as 10. Instrumentation 10 includes a first locking element in the form of a locking element 12 with a sleeve 12a, a spreading pin or rod 36 and a drill guide block 14. Also shown is a bone plate 16 including a plurality of holes 18 for receiving bone screws (not shown) at one end thereof. The bone plate 16 may be angled or bent to match the bone anatomy. The bone plate 16 may also include a hole 18a spaced intermediate the bone plate along a longitudinal axis of plate 16. All of the bone plate holes may have an internal circumferential area of reduced diameter formed from a circumferential radially inwardly extending rib or protrusion 52 having a wedge shape. Guide block 14 includes a plurality of holes 22 which are alignable with the holes 18 of the bone plate and are adapted to receive either locking element 12 or a drill guide so that pilot holes may be drilled in the bone (for example a radius) on which bone plate 16 is to be mounted. Also shown mounted in guide block 14 is a second locking element 24 which is insertable into hole 18a of bone plate 16. As shown locking element 24 may be permanently mounted in block 14 or may be a removeable locking element similar to locking element 12 located in bone 22a.

Referring to FIGS. 2-9 there is shown a first embodiment of a locking element generally denoted as 12 including an axially movable rod 36. Locking element sleeve 12a includes a bore 60 and an expandable tip 38 received in one of the bone plate holes 18 or 18a holds the block 14 on the bone plate 16.

Figure 2:
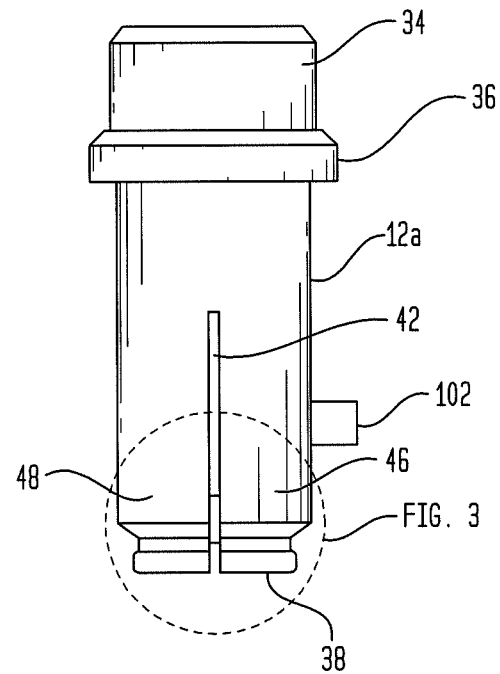
FIG. 2 is a side elevation view of the locking element and axially moveable rod of the present invention.
Figure 3:
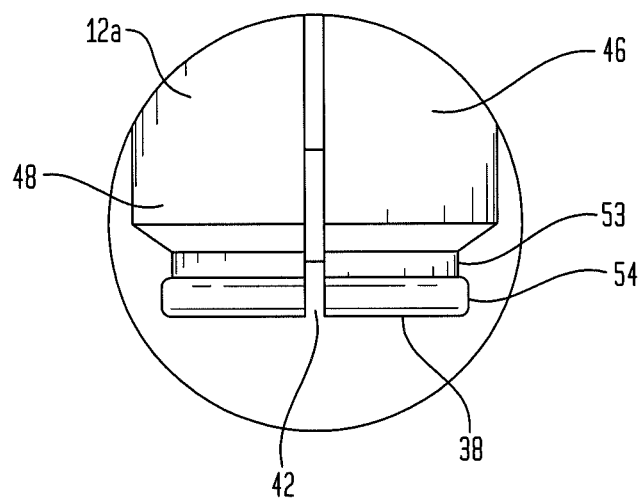
FIG. 3 is a partial cross-sectional view of the tip of the locking element of FIG. 2.
Figure 8:
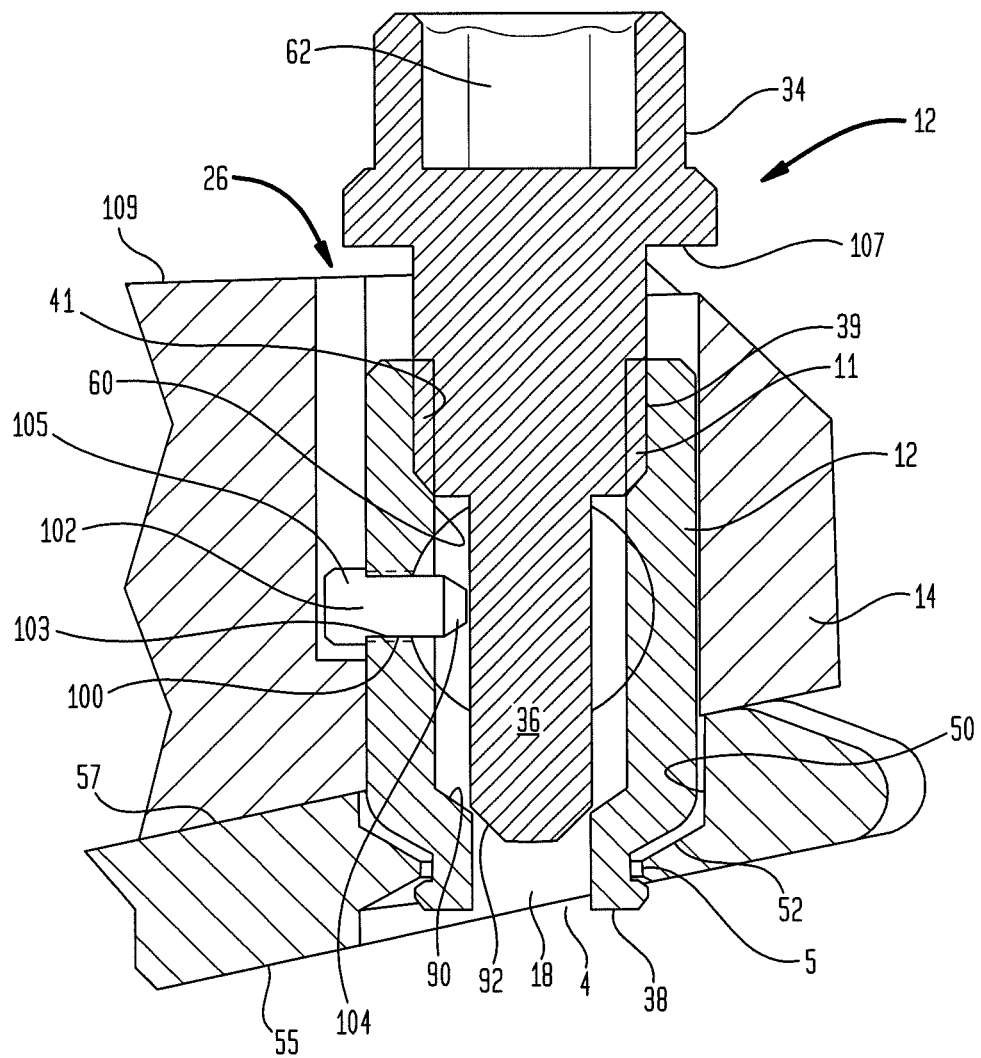
FIG. 8 is a cross-sectional view of the locking element and axially moveable rod of FIGS. 4-7 mounted in an aiming block and connected to a bone plate.

Referring to FIGS. 2 and 3 there is shown an elevation view of the assembled locking element 12 having sleeve 12a and axially moveable rod 36 of the present invention. Axially moveable rod 36 includes head 34 with a drive socket 62 and is threadably received within locking element sleeve 12a. As can be seen a slit 42 is provided in sleeve 12a so that tip 38 of locking element sleeve 12a can expand as the axially moveable rod 36 moves inwardly towards tip 38 upon rotation of head 34. Sleeve 12a has an anti-rotation element 102 adapted to be received within anti-rotation recesses 26 on the guide block 14 as shown in FIGS. 1A and 8. Anti-rotation element 102 includes a threaded shaft 100 insertable in a threaded bore 103 in sleeve 12a. Shown in FIG. 3 are the two bifurcated sections 46 and 48 of sleeve 12a formed by slit 42.

Referring again to FIG. 3 there is an enlarged view of the tip area 38 of locking element sleeve 12a shown in FIG. 2. This includes lip 54 and recessed area 53 that includes two of the bifurcated elements 46, 48.

Referring to FIGS. 4-7 axially moveable rod 36 includes a threaded section 39 which is engagable with a threaded section 41 in the upper end of bore 60 of locking element sleeve 12a. Thus by the rotation of head 34 axially moveable rod 36 may be moved into and out of engagement with a circumferential internal angled surface 90 of locking element sleeve 12a shown in FIG. 5.

Figure 4:
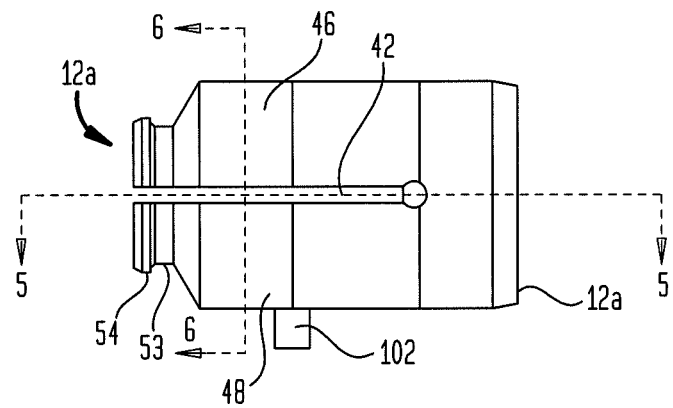
FIG. 4 is an elevation view of the bifurcated locking element of the present invention.
Figure 5:
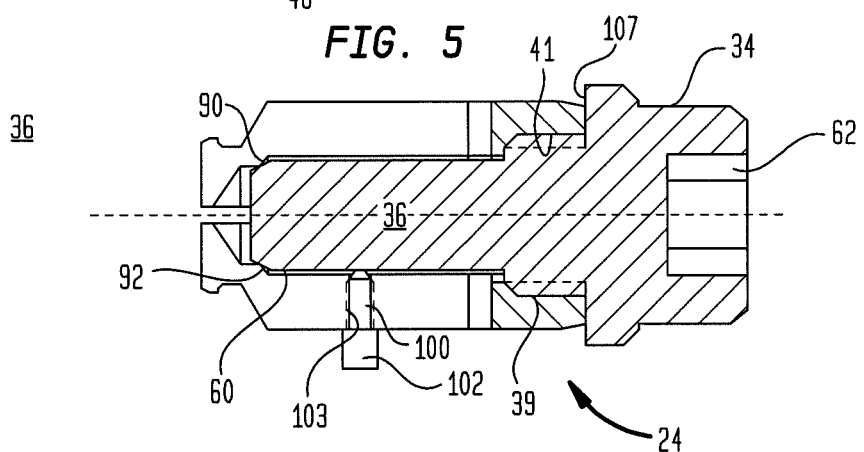
FIG. 5 is a cross-sectional view of the locking element of FIG. 4 with the axially movable rod threadably mounted therein.
Figure 7:
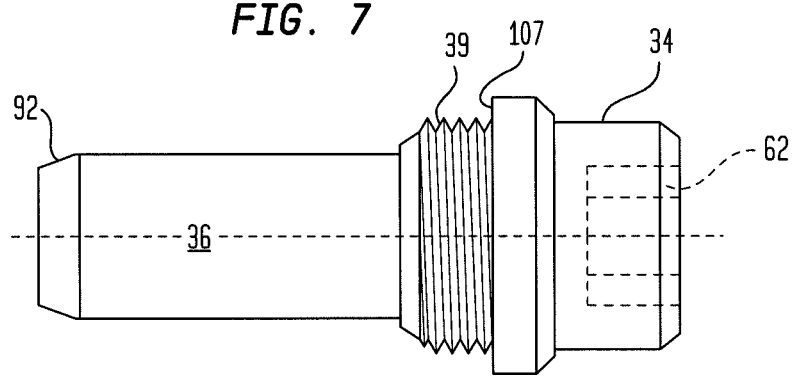
FIG. 7 is a side elevation view of the axially movable rod of the present invention.

Referring to FIG. 4 there is shown an elevation view of the locking element sleeve 12a with FIG. 7 showing an elevation view of the axially moveable rod 36 including a head 34 and threaded section 39 and angled or beveled end portion 92. Referring to FIG. 5 there is shown an assembly of the locking element sleeve 12a of FIG. 4 and the axially moveable rod 36 of FIG. 7 to form locking element 12 shown in cross-section. Referring to FIG. 7 there is a cross-sectional view of locking element 12 along lines 6-6 of FIG. 4 showing a pair of slots 42 and 44 forming four bifurcated segments 45, 46, 47 and 48. While four such segments are shown, two, three or more than four segments can be formed by the appropriate number of slots.

Referring to FIG. 8 there is shown a locking element 12 with the tip 38 of sleeve 12a expanded to engage a tip 51 of protrusion 52 in bone plate hole 18. This expansion is caused by movement of rod 36 axially downwardly such that surface 92 on axially movable rod 36 engages a stepped or slanted surface portion 90 on the inner bore 60 of locking element sleeve 12a. Locking element 12 also includes rotational stability pin 102 which has a head 105 and shaft 100 threadably mounted in bore 103 in the wall defining bore 60 of locking element sleeve 12a. Thus, by rotation of anti-rotation element 102 a tip 104 of anti-rotation element 102 can be moved transversely to an axis of bore 60. Head 105 of rotational stability pin 100 is received within slot 26 formed in the aiming block 14 to prevent rotation of locking element within the aiming block bore 18 when applying torque to head 34 of axially moveable rod 36.

Figure 6:
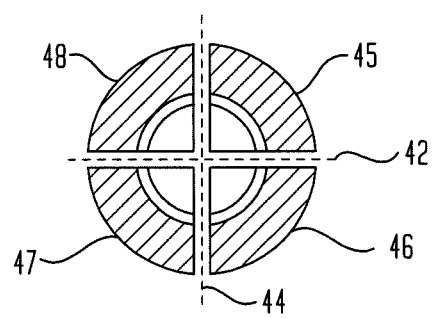
FIG. 6 is a cross-sectional view of the bifurcated locking element along lines 6-6 of FIG. 4.

Again referring to FIGS. 2-9 there is shown further details of the first locking element 12. This includes head or rotatable portion 34 which rotates threaded actuating rod 36 in threaded bore 60 best shown in FIGS. 2 and 8 which moves rod 36 axially within an expandable tip 38 of first locking element sleeve 12a. Sleeve 12a and rod 36 may be made of a metal or polymer such as PEEK. The expandable tip 38 has an internal stepped or angled surface 92 which engages a conical tip or angled surface 90 of rod 36. The expandable tip 38 can be bifurcated as shown in FIG. 6 and may contain three, four or even more branches. The branches are separated by slits or slots 42, 44 extending from an open end 43 of expandable tip 38 towards threaded portion 41. In the embodiment shown in FIGS. 4 and 6 there are two slits or slots 42 and 44 which form four tip branches 45, 46, 47 and 48. The slits or slots allow the branches to deform outwardly in a resilient fashion such that when the actuating rod 36 is moved out of engagement with stepped surface 92, the branches spring inwardly.

As best shown in FIGS. 2 and 8, bone plate 16 includes bores or holes 18 each having an inner wall 50 including a radially inwardly extending circumferential rib 52 having tip 51. Bone plate 16 has a bone contacting surface 55 and an opposite surface 57. In the embodiment as shown in FIGS. 2 and 8 the bone contacting surface 55 of the bone plate 16 surrounding hole 18 is recessed such that the rib 52 is located intermediate the outer bone plate surface 57 and the bone contacting bone plate surface 55. As best seen in FIG. 3 the end or tip 38 of first locking element 12 includes a lip 54 defining a recess 53 for receiving tip 51 of circumferential rib 52 of bone plate hole 18 inner wall 50. Inner bore 60 of the first locking element sleeve 12a is threaded at 41 to receive the threaded outer surface 39 on actuating rod or pin 36. Pin or rod 36 head 34 has a drive socket or other feature 62 which can be rotated using a standard tool (not shown) such as a hex drive. Rotation of rod 36 via head 34 rotates rod 36 moving it into and out of engagement with inner shoulder 90 of tip 38 and causes branches 45 through 48 to expand outwardly such that lip 54 engages tip 51 and locks the first locking element 12 and block 14 to bone plate 16 via rib 52 and head 34. Branches 45-48 are resilient and spring inwardly when rod 36 is moved out of engagement with surface 90.

Figure 9:
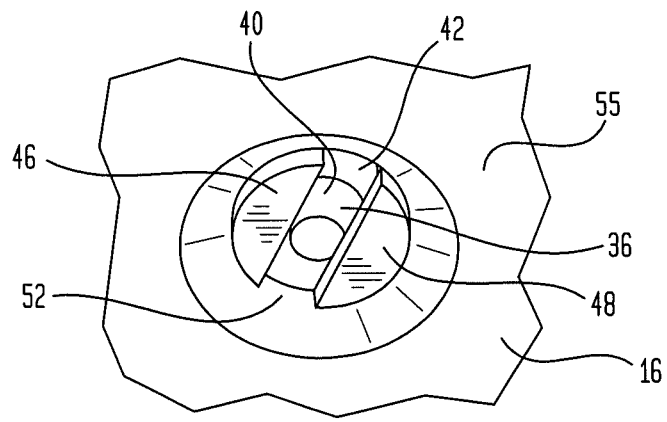
FIG. 9 is an isometric bottom view of the bone plate shown in FIG. 8 including the locking element and axially moveable rod of the present invention.

Referring to FIG. 9 there is shown a bottom view of the locking element 12 and axially movable rod 36 mounted in plate 16 with recess 53 engaging tip 51 of protrusion 52 of bone plate 16. As shown there are only two bifurcated elements 46 and 48 in FIG. 9.

Figure 10:
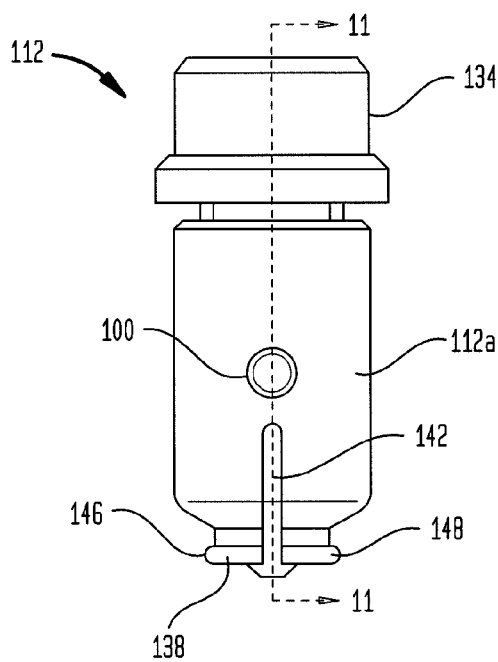
FIG. 10 is a side elevation view of the locking element and axially moveable rod of a second embodiment of the present invention in a first position.
Figure 11:
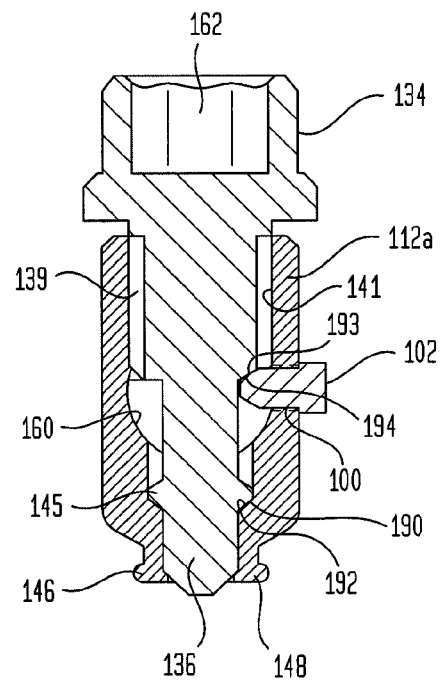
FIG. 11 is a cross-sectional view of the locking element and rod of FIG. 10 in the first position.

Referring to FIGS. 10-13 there is shown a second embodiment of the locking element generally denoted as 112 and a sleeve element 112a and axially movable rod 136 of the present invention. Referring to FIG. 10 there is shown a side elevation view of the second embodiment 112 with the axially movable rod 136 in a first position in which the bifurcated arms 146 and 148 of locking element sleeve 112a, which are identical to the bifurcated portions 46 and 48 of locking element sleeve 12a would be in an expanded position. Referring to FIG. 11 there is shown a cross-sectional view of FIG. 10 along lines 11-11 showing head 134 including head socket 162 of rod 136 in its position for expanding the bifurcated sections of locking element sleeve 112a. Again, axially moveable rod 136 includes a threaded portion 139 and the locking element sleeve 112a includes a threaded portion 141 which engage so that rotation of head 134 can move the rod 136 with respect to bore 160 of locking element sleeve 112a in an axial direction. As shown in FIG. 11 there is a first stop element 145 which protrudes outwardly of rod 136 and extends circumferentially therearound. Stop element 145 includes a downwardly facing circumferential surface 190 which can engage angled or slanted surface 192 of locking element sleeve 112a to expand the bifurcated tip 138 via slit or slot 142 of locking element sleeve 112a. The axially moveable rod 136 can have a second stop element or surface 194 engagable with upper surface 193 at tip 104 of anti-rotation pin 102. The engagement of surface 194 and upper surface 193 tip 104 limits the downward axial movement of rod 136 as shown in FIG. 11 thus placing a limit on the expansion of the bifurcated tip 138.

Figure 12:
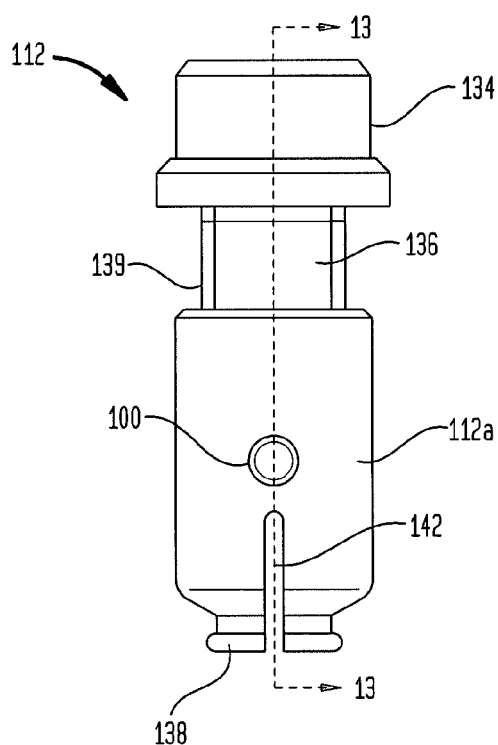
FIG. 12 is a side elevation view of the locking element and axially moveable rod of FIG. 10 in a second position.
Figure 13:
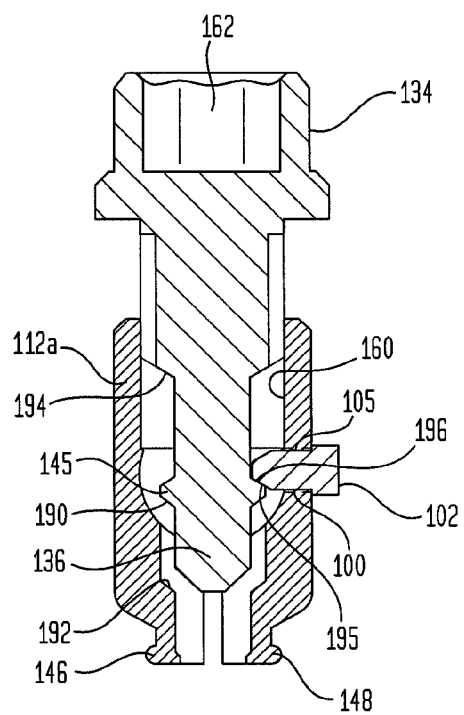
FIG. 13 is a cross-sectional view of the locking element and axially moveable rod of FIG. 12.

Referring to FIG. 12 there is shown the assembly of axially moveable rod 136 and locking element sleeve 112a with the axially moveable rod in a second retracted position within bore 160 of locking element sleeve 112a. Referring to FIG. 13 there is shown that, in this retracted position, the complete disassembly of rod 136 from locking element sleeve 112a is prevented by the engagement of an upwardly facing surface 196 of stop element 145 with the lower surface 195 tip 104 of anti-rotation element 102. Preferably anti-rotation element 102 includes a threaded section 100 which engages threaded bore 103 in locking element sleeve 112a so that by rotation of head 105 tip 104 may be moved axially out of bore 160 of locking element sleeve 112a. In this position rod 136 may either be inserted or removed from locking element sleeve 112a. Obviously the threaded portions 139 and 141 are sized to permit the engagement of surface 196 and tip 104 prior to the threads disengaging.

As shown in FIGS. 4-8 with the embodiment of rod 36 having no stop element 145 the length of rod 36 can be designed such that the engagement of bottom surface 107 of head 34 engages upwardly facing surface 109 of aiming block 14 to limit the expansion of bifurcated arms 45-48. In this embodiment the length of rod 36 will have to be sufficient so that recess 53 of the bifurcated tip 38 locks with tip 51 of bone plate protrusion 52 prior to surface 107 engaging surface 109. This has the added advantage of tightly clamping aiming block 14 to bone plate 16 by rotation of head 34 of axially moveable rod 36.

Figure 14:
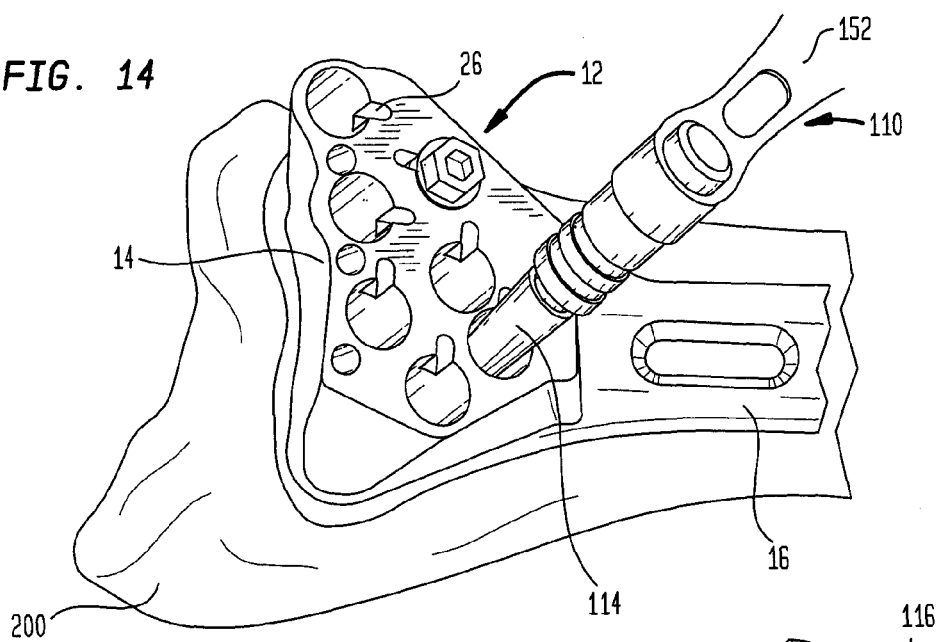
FIG. 14 shows the step of placing a drill guide in the guide block of the present invention being held in place by a locking element.
Figure 15:
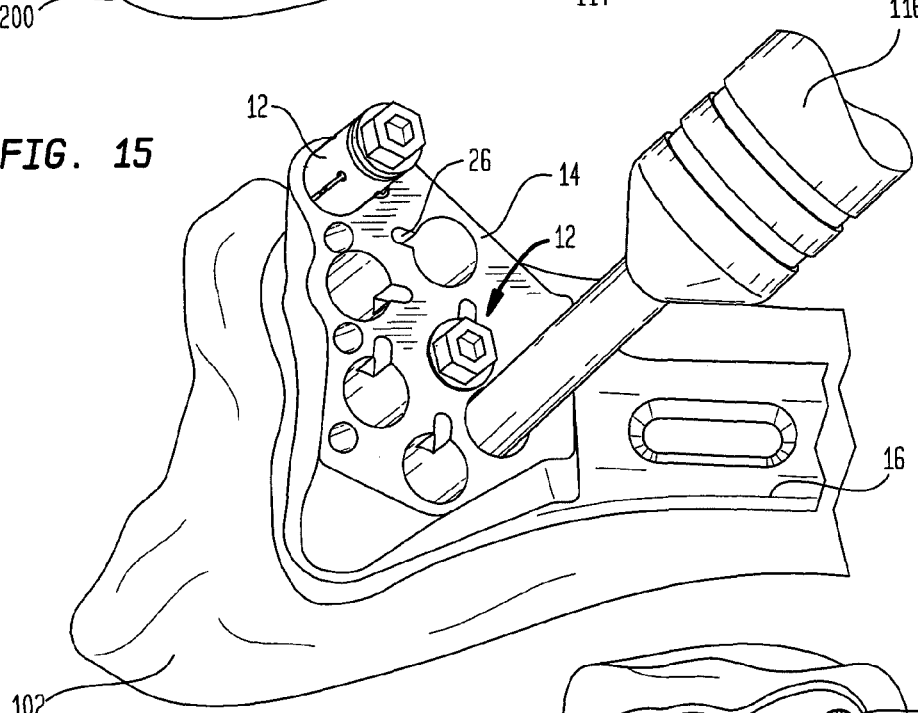
FIG. 15 shows the step of placing a drill guide in the guide block of the present invention having two locking elements and drilling a pilot hole.
Figure 16:
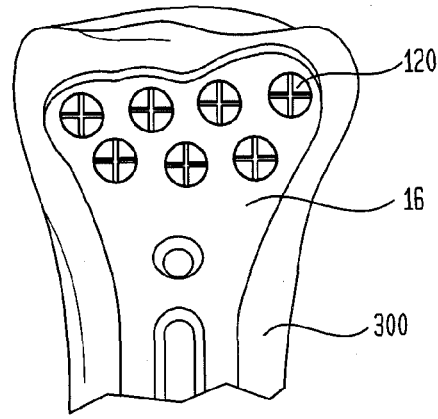
FIG. 16 shows a bone plate assembled to a distal radius with bone screws.

Referring to FIGS. 14-16 there is shown the method of forming pilot holes of the present invention. Initially, the bone plate 16 is located on an end of a long bone such as a radius 200 and the block 14 is placed on bone plate 16 with its guide bores 22 aligned with the holes 18 in plate 16. The guide block 14 is held onto the plate by the first and second locking elements 12 and 24 respectively with the first locking elements extending through one of the guide bores 22. Any convenient guide bore 22 may be chosen. As shown in FIG. 14 a drill guide 110 includes a handle 152 a tubular guide 114 which receives a drill bit (not shown). The drill bit may be powered by a pneumatic or electric drill and is adapted to form holes in the bone for bone screws as shown in FIG. 14. The drill guide is moved from one bore 22 to the next bore 22 and pilot holes are drilled in all the bone plate holes 18. The last pilot hole is drilled in the guide bore 22 which initially had the first locking element 12. Locking element 12 is placed in a guide bore which has been already used to drill a pilot hole and the drill guide is placed in the hole just vacated by first locking element 12 and that pilot hole is drilled.

Referring to FIG. 15 there is shown the use of two locking inserts 12 to hold the aiming block 14 to plate 16. In this case locking element 24 may be eliminated. Obviously in this case both locking elements 12 will have to be removed and relocated to drill all the pilot holes through bores 22 and 18. Also referring to FIG. 15 there is shown a depth gauge 116 of any conventional type and is used to measure the depth of the pilot hole drilled. If that hole is not drilled deeply enough the hole may be re-drilled using the drill guide 110.

FIG. 16 shows the plate 16 mounted on bone 200 with the bone screws 120 set in the plate 16 thereby locking the upper end of the plate to the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A drill guide system for a bone plate having holes therethrough for receiving bone screws, comprising:
    a guide block having at least two drill guide bores, each bore alignable with a bone screw receiving hole in a bone plate, the guide block having a first surface for contacting a surface of a bone plate and a second surface opposite the first surface;
    a locking element extending through a drill guide into the bone plate bone screw receiving bore, the locking element having a bore with a threaded portion and a bifurcated tip for engaging an inwardly extending protrusion on the wall of a bone screw receiving hole in the bone plate, the tip having an outwardly extending flange engaging a surface of the bone plate protrusion facing a bone contacting surface of the bone plate;
    an axially movable rod having a threaded portion mounted in the threaded bore portion of the locking element, the rod having a head engaging the second surface of the guide block and a tip engaging a bore in the tip of the locking element and capable of spreading sections of the bifurcated tip on axial movement of the rod prior to the rod head contacting the second surface of the aiming block, wherein the axially moveable rod has an outwardly extending first stop surface and wherein the locking element has a stop pin extending through a wall of the locking element in a direction transverse to the bore therein into the bore of the locking element, the locking element stop pin engageable with the axially moveable rod first stop surface on movement of the rod element head away from the second surface of the guide block.

2. The drill guide system as set forth in claim 1 wherein the stop pin on the locking element is moveable in the direction transverse to the bore in the locking element and is engageable with the first stop surface on the axially moveable rod in a first position and is not engagable with the first stop element in a second position.

3. A drill guide system for a bone plate comprising:
    a bone plate having an outer surface, a bone-contacting surface for application to a bone, first and second bone plate holes extending from the outer surface to the bone-contacting surface, and the first and second bone plate holes having a circumferential wall including an inwardly extending protrusion, the first bone plate hole extending along a first axis, the second bone plate hole extending along a second axis;
    an aiming block having an upper surface, a lower surface engageable with the outer surface of the bone plate, a first aiming block bore extending from the upper surface to the lower surface along an axis which is aligned with the first bone plate hole first axis, the aiming block having an additional bore extending from the upper surface to the lower surface having an axis aligned with the second bone plate hole for second axis;
    a locking element extending through an aiming block bore into the first bone plate hole, the locking element having a bore with a threaded bore portion and having a bifurcated tip portion for selectively engaging the inwardly extending protrusion;
    an axially moveable rod having a threaded portion mounted in the threaded bore portion of the locking element, the rod having a head with a surface for contacting the outer surface of the aiming block and an end portion for engaging a portion of the locking element bore in the bifurcated tip portion for separating sections of the bifurcated tip during axial movement of the rod prior to the head contacting the outer surface of the aiming block and a first stop surface intermediate the head and the tip portion; and a moveable stop pin mounted on the locking element selectively engageable with the stop surface on the rod.

4. The aiming block fixation system as set forth in claim 3, wherein the first and second bone plate holes are non-threaded.

5. The drill guide system as set forth in claim 3 wherein the moveable stop pin is mounted in a wall of the locking element and moveable in a direction transverse to the locking element bore through and into the bore, the locking element moveable stop pin engagable with the axially moveable rod first stop surface on movement of the rod element head away from the second surface of the guide block.

6. The drill guide system as set forth in claim 5 wherein the moveable stop pin on the locking element is moveable in a direction transverse to the bore in the locking element from a first to a second position and engages the first stop surface on the axially moveable rod in a first position and does not engage the first stop surface in the second position.

7. The drill guide system as set forth in claim 5 wherein the axially moveable rod has a second stop surface which engages the moveable stop pin on the locking element on movement of the rod element head towards the second surface of the guide block.

8. The drill guide system as set forth in claim 5 wherein the moveable stop pin has a head portion for engaging an anti-rotation recess in the aiming block bore.

9. The drill guide system as set forth in claim 3 wherein the bifurcated tip portion of the locking element has four sections separated by axially extending slits extending from the locking element tip towards the locking element head.

10. The drill guide system as set forth in claim 9 wherein the moveable stop pin is located between the locking element head and an end of the slits.

11. A drill guide system for a bone plate having holes therethrough for receiving bone screws, comprising:

a drill guide block having at least two drill guide bores, each bore alignable with a bone screw receiving hole in a bone plate, the guide block having a first surface for contacting a surface of a bone plate and second surface opposite the first surface;

a locking element extending through at least one drill guide block bore into the bone plate bone screw receiving hole, the locking element having an axially extending threaded bore portion and having a bifurcated tip surrounding the threaded bore portion, the bifurcated tip capable of engaging an inwardly extending protrusion formed on an internal wall of a bone screw receiving hole in the bone plate, the bifurcated tip having an outwardly extending flange engaging a surface of the protrusion facing a bone contacting surface of the bone plate;

an axially moveable rod having a thread mounted in the threaded bore portion of the locking element, the rod having a head for contacting the second surface of the guide block and an end portion engaging a portion of the bore in the bifurcated tip of the locking element for separating sections of the bifurcated tip on axial movement of the rod prior to the head contacting the second surface of the drill guide block, the axially moveable rod having a first stop surface formed thereon;

a moveable stop element is mounted in a wall of the locking element and moveable in a direction transverse to the locking element bore through and into the bore, the locking element stop element engagable with the axially moveable rod first stop surface on movement of the rod element head away from the second surface of the guide block.

12. The drill guide system as set forth in claim 11 wherein the moveable stop element extends in a direction perpendicular to an axis of the axially extending bore in the locking element.

13. The drill guide system as set forth in claim 12 wherein the bifurcated tip portion of the locking element has four sections separated by axially extending slits extending from the locking element tip towards the locking element head.

14. The drill guide system as set forth in claim 13 wherein the moveable stop element is located between the locking element head and an end of the slits.

15. The drill guide system as set forth in claim 14 wherein the axially moveable rod has a second stop surface which engages the moveable stop element on the locking element on movement of the rod element head towards the second surface of the guide block. surface which engages the moveable stop element on the locking element on movement of the rod element head towards the second surface of the guide block.

16. The drill guide system as set forth in claim 12 wherein the stop element on the locking element is moveable in a direction transverse to the bore in the locking element from a first postion to a second position and engages the first stop element on the axially moveable rod in the first position and does not engage the stop element in the second position.

17. The drill guide system as set forth in claim 16 wherein the moveable stop element has a head portion for engaging an anti-rotation feature in the aiming block bore.

18. The aiming block fixation system as set forth in claim 11, wherein the first and second bone plate holes are non-threaded.

* * * * *